US005750481A

United States Patent [19]

Del Vecchio et al.

[11] Patent Number: 5,750,481

[45] Date of Patent: May 12, 1998

[54] SOAPS PRODUCED FROM HIGH LAURATE CANOLA OIL-BASED FATTY ACIDS

[75] Inventors: Anthony J. Del Vecchio, Davis, Calif.; Eric Jungermann, Phoenix, Ariz.; Hemendra N. Basu, Bartlett, Ill.

[73] Assignee: Calgene, Inc., Davis, Calif.

[21] Appl. No.: 587,981

[22] Filed: Jan. 17, 1996

[51] Int. Cl.$^{6}$ .................................................. A61K 7/50

[52] U.S. Cl. .......................................... 510/152; 510/147

[58] Field of Search .................................... 510/147, 152

[56] References Cited

U.S. PATENT DOCUMENTS

| | | | |
|---|---|---|---|
| 2,820,768 | 1/1958 | Fromont et al. | 252/118 |
| 4,468,338 | 8/1984 | Lindberg | 510/147 |
| 4,985,170 | 1/1991 | Dawson et al. | 510/147 |
| 5,215,779 | 6/1993 | Dake et al. | 426/601 |
| 5,254,281 | 10/1993 | Pichardo et al. | 510/151 |
| 5,344,771 | 9/1994 | Davies | 435/172.3 |
| 5,387,362 | 2/1995 | Tollens et al. | 510/152 |
| 5,607,909 | 3/1997 | Kefauver et al. | 510/152 |

*Primary Examiner*—Jerry D. Johnson
*Attorney, Agent, or Firm*—Nikaido Marmelstein Murray & Oram LLP

[57] ABSTRACT

A mild, foaming soap produced by saponifying C12:0 fatty acids obtained from a plant having integrated into its genome a DNA sequence encoding C12:0 preferring acyl-ACP thioesterase.

20 Claims, No Drawings

SOAPS PRODUCED FROM HIGH LAURATE CANOLA OIL-BASED FATTY ACIDS

FIELD OF THE INVENTION

This invention relates to a soap product and a method of making the soap product; more specifically the invention relates to soaps prepared from laurate canola oils.

BACKGROUND OF THE INVENTION

Laurate canola oil (also LC-oil or lauric canola oil) is a product produced by the present assignee. Generally, it is a product similar to canola oil except that LC-oil contains lauric acid levels and myristic acid levels in weight percents greater than found in conventional canola oil; and compared to coconut oil, LC-oil contains lower levels of lower molecule weight fatty acids (C6, C8 and C10) and possesses a much higher level of unsaturation. Surprisingly, it now has been determined that soaps can be prepared with LC-oils having foaming and mildness properties that rival or best the properties of conventional consumer soap blends.

Soaps produced in the United States are generally made by one or two methods:

1. In a first method, oils and fats are boiled in an open kettle with caustic alkali solutions, bringing about saponification gradually until all of the fats and oils are completely saponified, followed by the removal of the glycerine. This process is either run in batch or in a continuous process.
2. In a second method, which is typically a continuous method (but may be run in batch), fatty acids and alkali are brought together in proper portions for complete saponification in a mixing valve or other device which brings them in intimate contact. The progress of saponification depends on the temperature, time of contact and efficiency of mixing.

Concentrated soap solutions are prepared by these methods. Such concentrated solutions are referred to as "neat" soaps, and they possess a concentration of 60–65% soap, about 35% water and traces of salt, and glycerine; these soaps are very viscous products. It is from this product that consumer soaps in the form of bars, flakes, granules and powders are produced, by first drying the neat soap into pellets having a moisture content of about 12–16% followed by finishing steps, such as milling, plodding, amalgamating, etc.

A consideration in selecting oils for making soap is that the soap preparation mixture contain the proper ratio of saturated and unsaturated, and long-and-short-chain fatty acids to result in a soap having the desired qualities of stability, solubility, ease of lathering, hardness, cleaning ability, etc. It has been determined that soaps prepared from fatty acid mixtures wherein a majority of the fatty acids in the mixtures have carbon chains of less than twelve atoms irritate skin. Soaps prepared from saturated fatty acids containing a majority of fatty acids with greater than eighteen carbon atoms in length are too insoluble for consumer use. Consumer bar soaps today are manufactured from coconut oil and/or tallow or their fatty acids. Palm kernel oil is sometimes substituted for coconut oil for economic reasons, and soaps prepared with palm kernel oil are adjusted for equivalent performances characteristics similar to non-substituted tallow/coconut formulations. Palm oil is often substituted for tallow.

Saponification of tallow produces a soap comprised of a mixture of fatty acids of C18:0, C16:0, C14:0 and C18:1 and saponification of coconut oil produces a soap comprised of a mixture of fatty acids of C12:0 and C14:0 (lauric acid and myristic acid respectively) and significant amounts of C8:0 and C10:0 fatty acids. Consumer soap preparations usually contain tallow/coconut (TC) ratio ranges from approximately 90:10 to 75:25.

Lauric acid is found only in the coconut fraction of T/C mixtures; thus, the most dramatic change observed in increasing the percent of the coconut fraction of T/C mixtures is the increase in the lauric acid. Increasing the coconut fraction in tallow/coconut fatty acid containing soaps generally improves the desirable foaming characteristics of such soaps, and in soaps with T/C ratios of 50:50 desirable skin mildness properties are reduced.

SUMMARY OF THE INVENTION

The present invention relates to soap compositions prepared by saponifying laurate canola oils (LC-oils) in combination with other oils such as palm and tallow. Laurate canola oils resemble canola oil except lauric canola oils contain lauric acid levels and myristic acid levels in weight percents greater than the weight percents of the fatty acids found in conventional canola oil. The LC-oil is used as a substitute for coconut oil and soaps prepared from LC-oil have been found to be milder to the skin and exhibit greater foaming characteristics than coconut based oils. The laurate canola oils are preferably produced in vivo by genetically engineered plants. Such plants produce seeds that preferentially accumulate oils with 12:0 fatty acids.

Thus, an object of this invention is to formulate consumer acceptable products produced with the LC oil or LC fatty acids.

It is still another object of the present invention to produce soaps from LC fatty acids that are competitive with coconut oil based soaps.

These and other objects are realized by reference to the detailed description of the invention set forth below.

DETAILED DESCRIPTION OF THE INVENTION

The terms referenced by abbreviation throughout the specification are shown here with their abbreviations: free fatty acids—FFA; fatty acid—FA; lauric or laurate canola—LC and triethanolamine—TEA; coconut oil-CNO; and coconut-coco.

It has now been found that the fatty acid compositions obtained from oils produced in accordance with the procedures set forth in U.S. Pat. No. 5,344,771 (herein incorporated by reference) differ from the fatty acid compositions obtained from canola oil (produced by industry today). In general, the fatty acid mixture obtained from the oils produced by the methods of the '771 patent contain greater amounts of lauric acid than conventionally produced canola oil and generally greater amounts of oleic and linoleic fatty acids than found in coconut oil. The oil produced by the methods set forth in the '771 patent is herein designated laurate canola oil (LC-oil) and the fatty acid compositions obtained from the oil are designated as laurate canola-oil based fatty acids.

The present inventors have now produced "neat" and diluted soap compositions by substituting laurate canola oils or fatty acids obtained therefrom for coconut based oils and their respective fatty acids.

The assignee of the present application, as disclosed in U.S. Pat. No. 5,344,771 has produced oils in vitro and in vivo that yield fatty acid compositions containing LC fatty acids. In the in vivo method a plant is altered by integrating into its genome a DNA construct having in the 5' to 3' direction of transcription, a transcriptional regulatory region functional in a seed cell of the plant, a translational regulatory region functional in the seed cell, a plant transit peptide encoding sequence, a DNA sequence encoding an *Umbellularia california* (bay) 12:0 preferring acyl-ACP thioesterase which is functional in the seed cell, and a transcriptional termination region functional in the seed cell.

Preferably, but without limitation the plants that are altered are oil producing plants of the Brassica family, including, but not limited to canola, rape and mustard. Other plants that may be genetically altered include soybean, peanut, safflower, etc.

The weight percent range of the fatty acid produced from LC-oil is shown in Table 1 below, which also compares the weight percent range of fatty acid from canola oil, coconut oil and palm kernel oil.

TABLE 1

| Common Name | Fatty Acid | Weight % in Laurate Canola | Weight % in Canola | Weight % Coconut Oil | Weight % in Palm Kernel Oil |
|---|---|---|---|---|---|
| caprylic | C8:0 | — | — | 8 | 3.5 |
| capric | C10:0 | — | — | 6 | 3.5 |
| lauric acid | C12:0 | 12–59 | — | 47 | 48.0 |
| myristic acid | C14:0 | ≦6 | <0.1 | 17.5 | 16.0 |
| palmitic acid | C16:0 | <6 | 4.0 | 9 | 8.0 |
| palmitoleic acid | C16:1 | <1 | 0.0 | — | 0 |
| stearic acid | C18:0 | <2.5 | 1.5 | 3 | 2.5 |
| oleic acid | C18:1 | 5–80 | 61.5 | 7 | 15.5 |
| linoleic acid | C18:2 | <40 | 20.0 | 2 | 2.5 |
| linolenic acid | C18:3 | <14 | 10.0 | — | 0 |
| arachidic acid | C20:0 | <1.0 | 0.5 | — | 0.1 |
| gadoleic acid | C20:1 | <2.0 | 1.0 | — | — |
| behenic acid | C22:0 | <1.0 | 0.3 | — | — |
| erucic acid | C22:1 | <2.0 | 0.1 | — | — |
| lignoceric acid | C24:0 | <0.2 | 0.2 | — | — |
| nervonic acid | C24:1 | <0.2 | — | — | — |

A typical fatty acid profile of LC-oil is set forth in column 2 of Table 2 below:

TABLE 2

| | % FA | % FA After Partial Hydrogenation |
|---|---|---|
| C10 | 0.1 | 0.1 |
| C12 | 38.8 | 38.8 |
| C14 | 4.1 | 4.1 |
| C16 | 2.7 | 2.9 |
| C16:1 | 0.2 | 0 |
| C18 | 1.6 | 32.8 |
| C18:1 | 32.8 | 20.0 |
| C18:2 | 11.2 | 0 |
| C18:3 | 6.8 | 0 |
| C20+ | 1.7 | 1.5 |

Although a typical fatty acid profile for LC-oil containing about 38 percent lauric acid is reported in Table 2, the percent lauric acid present in LC-oils can be obtained in amounts of up to 59% by weight (66 mole percent) with currently genetically engineered plants.

By the method set for in the '711 patent triglycerides are produced by enzymatic esterification of a glycerol moiety with lauric acid (and to a certain extent myristic acid) at only positions one and three. Thus, the hydroxyl group at the two position of the glycerol moiety is enzymatically non-equivalent to the hydroxyl groups at positions one and three. The amounts of lauric acid ultimately obtained from plant seeds can be increased (theoretically to 99 mole %) by also enzymatically esterifying the glycerol moiety at the two position with lauric acid. Genetically engineering plants with a DNA sequence encoding for plant hysophosphatidic acid acyltransferases, will accomplish this result and such methods are disclosed in U.S. application Ser. No. 08/327,451 filed Oct. 21, 1994 (WO 95/27791) herein incorporated by reference.

Thus, the amount of lauric acid set forth in Table 1 is merely for purposes of illustration and is not meant as a limitation.

A simple method for changing the composition of the fatty acids obtained from LC-oil is to hydrogenate the oil. Column 3 of Table 2 above shows the change in composition of the LC free fatty acid composition after hydrogenation. This composition too may be used to produce soaps and may be supplemented with all of the fatty acids obtained from LC-oil or supplemented with one or more of the isolated fatty acids of LC-oils obtained from the seeds harvested from genetically engineered plants. Thus, the upper value of C12 fatty acids is only limited by the imagination of the formulator.

From the fatty acid compositions mentioned above or from the oils of the genetically engineered seeds, neat soap solutions, liquid soaps and bar soaps can be prepared and examples are set forth below:

EXAMPLES

Example 1

Obtaining LC-oil

The seeds produced from plants with altered genomes are harvested, and pressed to yield oils containing glycerides of LC fatty acids. The fatty acids can be obtained by refluxing the laurate canola oil with alcoholic KOH (or a variety of other bases), for about one hour, and the alcohol is mostly distilled off. The residue is dissolved in hot water and acidified with, for instance 10% sulfuric acid, but other acids may be used. The produced fatty acids rise to the top, leaving the aqueous gycerol behind, and are separated by flowing them over a baffle. The acids are then washed with distilled water until neutral. The water is allowed to drain and the acids are dried with anhydrous sodium sulfate. Decanting follows.

Example 3

Preparation of "neat" soap

Neat soaps were prepared by neutralizing the following fatty acid mixtures with calculated amounts of 50% caustic soda solution: i) 80:20 tallow fatty acids:coco fatty acids; ii) 80:20 tallow fatty acids:LC fatty acids and iii) 50:50 tallow fatty acids:LC fatty acids superfatted with 7% tallow fatty acid. Superfatting includes the step of adding fatty acids to a soap composition to counteract the skin-drying effect of soap to provide a moisturizing effect and to improve foam quality. The LC fatty acids present in the prepared soaps possessed the fatty acid profile shown in Column 2 of Table 2. The fatty acid mixtures were heated to about 75° C. and the caustic was added with vigorous stirring. Temperatures were allowed to rise to 105° C. Small quantities of water and about 0.5% sodium chloride and glycerine were added. At this temperature, very viscous, but stirrable soap solutions were obtained, containing 60–65% saponified products, after about twenty minutes of mixing.

Example 4

Soap Pellets

The "neat" soap solution of Example 3 was placed onto aluminum trays and dried in a convection oven at 105° C. until dry soap was formed. The resultant soaps were compared for color and physical properties with soap made from CNO fatty acids and found to be of similar quality. All of the soaps possessed acceptable colors and above all, the coconut fatty acid and the LC fatty acid based soaps could be handled using the same processing procedures.

Examples 5–8

Preparations of TEA base Soaps

U.S. Pat. No. 2,820,768, herein incorporated by reference, discloses the production of mild transparent soaps sold under the trade name NEUTROGENA®. The transparent soaps produced herein were prepared by mixing the oils shown in Table 3 below and tallow fatty acids in triethanolamine (TEA) in the amounts as shown in Table 3. The LC oils possessed the fatty acid profiles shown in Column 2 of Table 2. Excess NaOH was added to the mixture to convert the oils and the fatty acids to soap. Stearic acid was then added to neutralize the excess NaOH and TEA to form a TEA—stearate soap. Additional glycerine was then added. The hot liquid soaps were then poured into molds, allowed to set up to bars by cooling and were examined. Examples #5 and #6 allow a direct comparison of the effect of substituting an LC-oil for coconut oil. Example #7 explores alternative compositions of LC-soap compositions. And Example #8 shows that production of bar soaps from the partially hydrogenated LC soil shown in Column 3 of Table 2.

TABLE 3

| | Example # | | | |
|---|---|---|---|---|
| Ingredients | #5 | #6 | #7 | #8 |
| Hydrogenated LC oil | | | | 50.0 g |
| Tallow Fatty Acid | 33.0 g | 33.0 g | 0 | |
| Castor Oil | 15.0 g | 33.0 g | 35.0 g | 15.0 g |
| Coconut Oil | 20.0 g | 0 | 0 | |
| LC Oil | 0 | 20.0 g | 35.0 g | |

TABLE 3-continued

| | Example # | | | |
|---|---|---|---|---|
| Ingredients | #5 | #6 | #7 | #8 |
| Sodium Hydroxide (50%) | 24.5 g | 24.5 g | 25.0 g | 25.0 g |
| TEA (99%) | 100.0 g | 100.0 g | 100.0 g | 100.0 g |
| Stearic Acid | 52.0 g | 52.0 g | 17.0 g | 17.0 g |
| Glycerine | 24.0 g | 24.0 g | 20.0 g | 20.0 g |
| Water | 13.5 g | 13.5 g | 10.0 g | |

Solid transparent bars were obtained in all Examples 5–8. Soap bars #5 and #6 and #8 solidified at room temperature; soap bar #7 solidified on refrigeration, but remained solid once it had set up

Examples 9–20

An additional twelve sets of bar soap formulations were prepared (See Tables 4A and 4B). Each set consisted of an A and a B series. The "A" series compositions were based on coconut oil. The "B" series compositions were based on LC-oil. Two modifications were made to these bar soap compositions, relative to the compositions shown in Table 3: i) tallow oil was used instead of the fatty acids derived from the tallow oil and ii) 85% TEA was used instead of 99% TEA.

Oils and the TEA were weighed into a beaker and heated to 50°–60° C. Required amounts of 33% caustic (see Tables 4A and 4B) were added slowly and the temperature was allowed to rise to about 90° C. The solution was maintained at a temperature range of 90°–100° C. with constant stirring for 15 minutes. Glycerine and molten stearic acid were added and the solution was left at 90°–100° C. for another 10 minutes. The solution was then poured into molds and allowed to solidify. The formulations are set forth in Tables 4A–4B.

TABLE 4A

| Ingredients | 9A | 9B | 10A | 10B | 11A | 11B | 12A | 12B | 13A | 13B | 14A | 14B |
|---|---|---|---|---|---|---|---|---|---|---|---|---|
| TEA | 32.8 | 32.8 | 28 | 28 | 28 | 28 | 28 | 28 | 28 | 28 | 28 | 28 |
| Castor Oil | 5 | 5 | 5 | 5 | 2.4 | 2.4 | 0 | 0 | 0 | 0 | 0 | 0 |
| Coconut Oil | 6.8 | 0 | 11.6 | 0 | 12.9 | 0 | 14.1 | 0 | 17.1 | 0 | 18.5 | 0 |
| LC Canola | 0 | 6.8 | 0 | 11.6 | 0 | 12.9 | 0 | 14.1 | 0 | 17.1 | 0 | 18.5 |
| Tallow | 11.6 | 11.6 | 11.6 | 11.6 | 12.9 | 12.9 | 14.1 | 14.1 | 17.1 | 17.1 | 19.6 | 19.6 |
| NaOH 33.3% | 12.5 | 12.5 | 13.8 | 13.8 | 13.8 | 13.8 | 13.8 | 13.8 | 13.8 | 13.8 | 16 | 16 |
| Water | 20 | 20 | .7 | .7 | 0.7 | 0.7 | 0.7 | 0.7 | 0.7 | 0.7 | 0 | 0 |
| Stearic Acid | 21 | 21 | 21 | 21 | 21 | 21 | 21 | 21 | 15 | 15 | 10 | 10 |
| Glycerine | 8.3 | 8.3 | 8.3 | 8.3 | 8.3 | 8.3 | 8.3 | 8.3 | 8.3 | 8.3 | 8.3 | 8.3 |
| Results/Properties | | | | | | | | | | | | |
| pH, 1% | 8.85 | 9 | 8.75 | 8.85 | 8.77 | 8.7 | 8.7 | 9.01 | 9.09 | 9.16 | 9.19 | 9.18 |
| % Stearic Acid* | 19.5 | 15 | 20.1 | 18.8 | 20.3 | 19. | 24.8 | 8.12 | 14.9 | 16.6 | 11.3 | 9.9 |
| Foam Test 0 ppm (A) | 90 | 105 | 85 | 115 | 100 | 110 | 80 | 5 | 125 | 100 | 155 | 170 |
| Foam Test 50 ppm (B) | 70 | 90 | 65 | 95 | 95 | 105 | 65 | 95 | 70 | 80 | 85 | 95 |

*All values are percents by weight, unless otherwise indicated (e.g. foaming is reported in milliliters). The stearic acid shown at the bottom portion of the table represents a titrated amount present in final soap compositions.
(A) 5 ml of 5% solution
(B) 10 ml of 5% solution.

TABLE 4B

| Ingredients | 15A | 15B | 16A | 16B | 17A | 17B | 18A | 18B | 19A | 19B | 20A | 20B | Molten Neutrogena |
|---|---|---|---|---|---|---|---|---|---|---|---|---|---|
| TEA | 28 | 28 | 18 | 18 | 23 | 23 | 29 | 29 | 25 | 25 | 20 | 20 | |
| Castor Oil | 0 | 0 | 0 | 0 | 0 | 0 | 0 | 0 | 0 | 0 | 0 | 0 | |
| Coconut Oil | 7.8 | 0 | 8.8 | 0 | 8.2 | 0 | 8.2 | 0 | 9 | 0 | 0 | 0 | |
| LC Canola | 0 | 7.8 | 0 | 8.8 | 0 | 8.2 | 0 | 8.2 | 0 | 9 | 10 | 0 | |
| Tallow | 31.4 | 31.4 | 35.2 | 35.2 | 33.3 | 33.3 | 33.3 | 33.3 | 36 | 36 | 0 | 10 | |
| NaOH 33.3% | 16.5 | 16.5 | 20 | 20 | 18 | 18 | 16.5 | 16.5 | 18 | 0 | 18.5 | 18.5 | |
| Water | 0 | 0 | 0 | 0 | 0 | 0 | 0 | 0 | 0 | 5 | 0 | 0 | |
| Stearic Acid | 10 | 10 | 10 | 10 | 10 | 10 | 5 | 5 | 5 | 7 | 5 | 5 | |
| Glycerine | 6.3 | 6.3 | 8.3 | 8.3 | 7.5 | 7.5 | 8 | 8 | 7 | 0 | 6.5 | 6.5 | |
| Results/Properties | | | | | | | | | | | | | |
| pH, 1% | 9.37 | 9.25 | 9.4 | 8.7 | 9.52 | 9.39 | 9.8 | 9.8 | 9.34 | 9.55 | 9.15 | 8.95 | 9.2 |
| % Stearic Acid* | 9.9 | 11.7 | 10.3 | 8.0 | 10.05 | 8.5 | 8.9 | 8.9 | 5.7 | 5.45 | 5.66 | 5.39 | 18.2 |
| Foam Test 0 ppm (A) | 170 | 180 | 165 | 200 | 165 | 190 | 155 | 165 | 130 | 185 | 130 | 170 | 120 |
| Foam Test 50 ppm (B) | 100 | 140 | 110 | 90 | 105 | 130 | 90 | 110 | 100 | 110 | 65 | 130 | 70 |

*By analysis of finished soap bars (also applies to Examples 9–14).
(A) 5 ml of 5% solution
(B) 10 ml of 5% solution.

In series 9–15 and 17–19 translucent soap bars were formed. In series 16, the solutions became viscous, foamed and became difficult to handle, and in series 20 solid to slightly foamy compositions were obtained.

In all cases, soaps of series B, i.e., soaps prepared from LC oil acids exhibited better foaming results than series A soaps prepared with coconut oil.

The foam test reported above and elsewhere herein includes placing 200 ml of water of the appropriate hardness to be tested (either 0 ppm or 50 ppm) into a 500 ml graduated extraction cylinder. An aliquot of soap solution (5 ml for the 0 ppm test; 10 ml for the 50 ppm test) is added without causing foaming. Then 1 ml of olive oil is added using a pipette and distilled water is added to bring the total volume to 250 ml. The cylinder is stoppered and is gently inverted ten times in 25 seconds, and an immediate reading is taken. Foam height reported is the actual foam height reached, in milliliters minus 250 ml.

Examples 21–29

In another series of experiments, nine soap solutions were prepared from 100% tallow fatty acid, 100% coconut fatty acid and 100% LC fatty acid and soaps solutions with varying T/C ratios and varying T/LC ratios were prepared as shown in Table 6. The LC-oil from which the soaps were prepared possessed the fatty acid profile set forth in Column 2 of Table 2.

Commercial grades of tallow fatty acid and coconut fatty acid were used. The LC fatty acid was prepared by refluxing LC oil with alcoholic KOH for one hour, diluting with water and splitting to obtain the corresponding fatty acid by reaction with dilute sulfuric acid followed by washing and drying.

TABLE 5

| Example | | Analysis | | Foam | | Mildness |
|---|---|---|---|---|---|---|
| No. | Soap From | pH, 1% | F.F.A. | 0 ppm | 50 ppm | Score |
| 21 | 100% Tallow | 9.60 | .019 | 170–185 | 120–125 | 4.07 |
| 22 | 90/10 T:C | 9.58 | .020 | 175–185 | 100 | 2.50 |

TABLE 5-continued

| Example | | Analysis | | Foam | | Mildness |
|---|---|---|---|---|---|---|
| No. | Soap From | pH, 1% | F.F.A. | 0 ppm | 50 ppm | Score |
| 23 | 80/20 T:C | 9.50 | .020 | 155–160 | 110 | 2.79 |
| 24 | 50/50 T:C | 9.60 | .019 | 140–145 | 75–80 | 4.29 |
| 25 | 100% fatty acid C | 9.55 | .019 | 60–65 | 0 | 18.07 |
| 26 | 100% fatty acid LC | 9.60 | .019 | 195–200 | 65 | 6.43 |
| 27 | 90/10 T:LC | 9.58 | .019 | 195–200 | 105–110 | 2.57 |
| 28 | 80:20 T:LC | 9.57 | .019 | 200–205 | 130–145 | 2.79 |
| 29 | 50:50 T:LC | 9.60 | .020 | 165–175 | 90–95 | 2.50 |

T = Tallow fatty acid;
C = Coconut fatty acid; and
LC = Lauric fatty acids.

All the samples were prepared as relatively dilute solutions. The foam tests were run on 5% soap solutions using distilled water (0 ppm) and hard water (50 ppm Mildness tests were run on 8% soap solutions and in accordance with a modified procedure of Frosch, Peter J. et al. "The Soap Chamber Test," Journal of the American Academy of Dermatology, Vol. I (July 1979), pp. 35–41 (herein incorporated by reference). The modified procedure uses a totally occlusive plastic cup, 19 mm in diameter as a delivery system for testing the soaps on the skin of volunteers. Cotton cloth (WEBRIL) was snugly fit into the cup and received approximately 0.1 ml of each solution by pipette. The cup was sealed, by using non occlusive tape, to one of ten sites on the right and left paraspinal areas of the volunteers. Test products were rotated among the ten sites.

The mildness tests shown in the above Table 5 represent averages of the total scores from fourteen subjects rated on three criteria: erythema, scaling and fissures. The lower scores identify milder products. The 100% laurate canola oil soap (Example 26) shows two distinct advantages over 100% coconut oil soap (Example 25): i) it has better foaming properties and ii) it is significantly milder. These benefits carry through to mixed soaps containing tallow, especially at the higher coconut and LC levels.

Soaps made with LC fatty acids produced significantly better foams than those made with coconut fatty acids. The improvement in foamability is carried through to blends of these fatty acids with tallow fatty acids where laurate canola fatty acids comprise the lower blend ratio values of the final soap.

Preparation of "neat" soap samples using LC-fatty acids and blends with tallow fatty acids all exhibited acceptable colors, and are handled the same way as tallow/coconut fatty acid based soaps.

Although the foregoing invention has been described in some detail by way of illustration and example for purposes of clarity and understanding, it will be obvious that certain changes and modifications may be practiced within the scope of the appended claims. For instance, the soap compositions of this invention may include perfumes, coloring agents, opacifiers, antioxidants, antibacterial agents, emollients, etc. Although various bar soaps composition have been described and their percent soap composition is described, the invention is not limited to soaps containing a particular percent soap. Thus, soaps can be prepared containing 1% to 100% soap, depending upon moisture content and additives identified above.

What is claimed is:

1. A soap comprising saponified products of a laurate canola oil.

2. The soap of claim 1, comprising about 1–100% by weight of saponified products.

3. The soap of claim 1 wherein the saponified products of laurate canola oil contain at least 12% of the salt of lauric acid.

4. The soap of claim 3, wherein the saponified products contain approximately 6% by weight or less of the salt of myristic acid.

5. The soap of claim 1, containing between 60 to 65% by weight of saponified laurate canola oil products.

6. The soap of claim 1 in solid form.

7. The soap of claim 1 in solution form.

8. The soap of claim 1 which is transparent.

9. The soap of claim 1, wherein at least 50% by weight of the saponified products is obtained from tallow fatty acids.

10. The soap of claim 9, wherein 50–90% by weight of the saponified products is obtained from tallow fatty acids.

11. The soap of claim 1 wherein said saponified products of the laurate canola oil contain at least 0.1% and up to 6% by weight of the salt of myristic acid.

12. The soap of claim 1 wherein saponified products of laurate canola oil do not include C8 and C10 fatty acids.

13. A soap comprising hydrogenated products of laurate canola fatty acids.

14. A soap obtained by saponifying laurate canola oil.

15. A soap obtained by a process, comprising the steps of:

producing C12:0 fatty acids in a plant seed cell by growing a plant having integrated into its genome a DNA construct, the construct comprising in the 5' to 3' direction of transcription, a transcriptional regulatory region functional in the plant seed cell, a translational regulatory region functional in the plant seed cell, a plant transit peptide encoding sequence, a DNA sequence encoding C12:0 preferring acyl-ACP thioesterase functional in the plant seed cell and a transcription termination region functional in the plant seed cell;

recovering the fatty acid containing oil of the seed cell and saponifying said oil or the fatty acids obtained from said oils.

16. The soap according to claim 15, wherein said plant is Brassica and the preferential acyl ACP thioesterase functional in said seed cell is an *Umbellularia california* C12:0 preferring acyl ACP thioesterase.

17. A method of increasing the foaming properties of tallow/coconut blend soaps by replacing coconut saponification products comprising:

formulating tallow blend soaps with saponification products of laurate canola oil.

18. The method of claim 17 wherein said saponification products of laurate canola oil comprise the salts of the fatty acids having the following carbon chainlengths and unsaturation in the weight percents shown

| | |
|---|---|
| C10 | 0.1% |
| C12 | 38.8% |
| C14 | 4.1% |
| C16 | 2.7% |
| C16:1 | 0.2% |
| C18 | 1.6% |
| C18:1 | 32.8% |
| C18:2 | 11.2% |
| C18:3 | 6.8% |
| C20+ | 1.7% |

19. A method for improving mildness properties of tallow blend soaps comprising: formulating tallow blend soaps with an effective amount of at least one member selected from the group consisting of saponified laurate canola oil, saponified laurate canola fatty acids and hydrogenated and saponified laurate canola fatty acids.

20. A soap comprising saponified products of a laurate canola oil, said saponified products of the laurate canola oil contain at least 12% by weight of the salt of lauric acid, and 6.0% or less of the salt of myristic acid.

* * * * *